United States Patent
Schelwies et al.

(10) Patent No.: US 12,172,956 B2
(45) Date of Patent: Dec. 24, 2024

(54) METHOD FOR THE ISOMERIZATION OF A 3-(Z)-UNSATURATED CARBOXYLIC ACID TO THE 3-(E)-ISOMER

(71) Applicant: BASF SE, Ludwigshafen am Rhein (DE)

(72) Inventors: Mathias Schelwies, Ludwigshafen am Rhein (DE); Wolfgang Siegel, Ludwigshafen am Rhein (DE); Rocco Paciello, Ludwigshafen am Rhein (DE); Andreas Keller, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 1083 days.

(21) Appl. No.: 16/969,680

(22) PCT Filed: Feb. 13, 2019

(86) PCT No.: PCT/EP2019/053599
§ 371 (c)(1),
(2) Date: Aug. 13, 2020

(87) PCT Pub. No.: WO2019/158611
PCT Pub. Date: Aug. 22, 2019

(65) Prior Publication Data
US 2021/0009495 A1 Jan. 14, 2021

(30) Foreign Application Priority Data
Feb. 13, 2018 (EP) .................................... 18156469

(51) Int. Cl.
| C07C 51/353 | (2006.01) |
| C07C 51/09 | (2006.01) |
| C12P 7/6427 | (2022.01) |
| C12P 7/6436 | (2022.01) |

(52) U.S. Cl.
CPC ............. *C07C 51/353* (2013.01); *C07C 51/09* (2013.01); *C12P 7/6427* (2013.01); *C12P 7/6436* (2013.01); *C07B 2200/09* (2013.01)

(58) Field of Classification Search
CPC ....... C07C 51/353; C07C 51/09; C07C 57/03; C07C 45/76; C07B 2200/09
See application file for complete search history.

(56) References Cited

U.S. PATENT DOCUMENTS

| 2020/0055834 A1 | 2/2020 | Schelwies et al. |
| 2020/0123586 A1 | 4/2020 | Siegel et al. |

FOREIGN PATENT DOCUMENTS

| WO | WO-9206063 A3 | 8/1992 |
| WO | WO-2014079691 A1 | 5/2014 |
| WO | WO-2018154048 A1 | 8/2018 |
| WO | WO-2018153727 A3 | 10/2018 |
| WO | WO-2020058505 A1 * | 3/2020 |

OTHER PUBLICATIONS

Kim et al., Palladium (II) catalyzed isomerization of olefins with tributltin hydride, Journal of Organic Chemistry, vol. 72, No. 14, pp. 5424 5426 (Year: 2007).*
Yus et al., Comounds with all-carbon functions, Science of Synthesis, vol. 47: Alkenes, Georg Thieme Verlag KG, Stuttgarg, Germany, p. 1076 (Year: 2009).*
Gano, J., et al., "A New Method for Predicting Isomerization Barriers in Sterically Congested Alkenes from the First Correct Barrier Measurement in Solution: (Z)-2,2,3,4,5,5-Hexamethyl-3-hexene", Journal of Organic Chemistry, vol. 52, No. 25, 1987, pp. 5636-5638.
International Search Report for PCT/EP2019/053599 mailed May 14, 2019.
Kim, I.S., et al., "Paladium(II)-Catalyzed Isomerization of Olefins with Tributyltin Hydride", Journal of Organic Chemistry, vol. 72, No. 14, 2007, pp. 5424-5426.

(Continued)

*Primary Examiner* — Yate' K Cutliff
(74) *Attorney, Agent, or Firm* — Faegre Drinker Biddle & Reath LLP

(57) ABSTRACT

The present invention relates to a method for isomerizing a 3-(Z)-unsaturated carboxylic acid of the formula 1-Z or a salt thereof, wherein $R^2$ is $C_1$-$C_{24}$-alkyl, $C_2$-$C_{24}$-alkenyl having 1, 2, 3 or more than 3 C—C double bonds, unsubstituted or substituted $C_5$-$C_{12}$-cycloalkyl, or unsubstituted or substituted aryl; $R^1$ is hydrogen or has one of the definitions specified for $R^2$; with the proviso that $R^2$ has a higher priority than $R^1$ in accordance with IUPAC; to give a 3-(E)-unsaturated carboxylic acid of the formula I-E or a salt thereof, wherein the isomerization of the compound of the formula 1-Z is effected in the presence of an anhydride of an organic acid and a base or in the presence of a ketene of formula $CR^{11}R^{12}C(0)$, wherein $R^{11}$ and $R^{12}$ are as defined in the claims and in the specification and a base. In particular, the present invention relates to a method for preparing compositions with increased content of (3E,7E)-homofarnesylic acid starting from compositions comprising (3Z,7E)- and (3E,7E)-homofarnesylic acid.

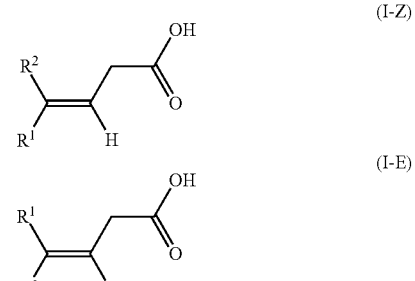

13 Claims, No Drawings

(56) References Cited

OTHER PUBLICATIONS

Larionov, E., et al., "Scope and Mechanism in Palladium-Catalyzed Isomerizations of Highly Substituted Allylic, Homoallylic, and Alkenyl Alcohols", Journal of the American Chemical Society, vol. 136, No. 48, 2014, pp. 16882-16894.

Li, H., et al., "Iridium-Catalyzed Selective Isomerization of Primary Allylic Alcohols", Accounts of Chemical Research, vol. 49, No. 1, 2016, pp. 1232-1241.

Written Opinion of the International Searching Authority for PCT/EP2019/053599 mailed May 14, 2019.

Yus, M., et al., "Compounds with All-Carbon Functions", Science of Synthesis, vol. 47: Alkenes, Georg Thieme Verlag KG, Stuttgart, Germany, 2009, p. 1076.

\* cited by examiner

METHOD FOR THE ISOMERIZATION OF A 3-(Z)-UNSATURATED CARBOXYLIC ACID TO THE 3-(E)-ISOMER

CROSS-REFERENCE TO RELATED APPLICATIONS

This application is a national stage application (under 35 U.S.C. § 371) of PCT/EP2019/053599, filed Feb. 13, 2019, which claims benefit of European Application No. 18156469.1, filed Feb. 13, 2018, both of which are incorporated herein by reference in their entirety.

BACKGROUND OF THE INVENTION

The present invention relates to a method for the isomerization of a 3-(Z)-unsaturated carboxylic acid to a 3-(E)-unsaturated carboxylic acid in the presence of a base and acylating agent such as an anhydride of an organic acid or a ketene compound, especially a method for preparing compositions with increased content of (3E,7E)-homofarnesylic acid starting from compositions comprising (3Z,7E)- and (3E,7E)-homofarnesylic acid.

PRIOR ART

The carbonylation products of allyl alcohols are valuable intermediates for preparing numerous commercial products. By means of carbonylation of the allyl alcohols nerolidol and farnesol, for example, carboxylic acids can be obtained which, after reduction to the corresponding alcohols, can be cyclized to give valuable aroma chemicals. For instance, (3E,7E)-homofarnesylic acid, from the carbonylation of E-nerolidol, can be subjected to a reduction to obtain (3E, 7E)-homofarnesol

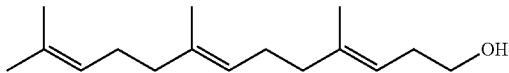 [SMILES: CC(C)=CCC/C(C)=C/CC/C(C)=C/CCO]

and this can be further subjected to a cyclization to obtain (−)-ambrox.

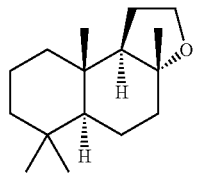

(−)-Ambrox is an important aroma chemical and (3E,7E)-homofarnesylic acid is therefore an important intermediate for preparing (−)-ambrox.

Various methods are described in the literature for directly preparing (3E,7E)-homofarnesylic acid. Compositions comprising (3E,7E)- and (3Z,7E)-homofarnesylic acid are industrially available and inexpensive.

WO 2014/079691, for example, describes a method for preparing E/Z-homofarnesylic acid by carbonylation of ß-farnesene in the presence of water and a palladium dichloride complex comprising phosphine ligands.

WO 92/06063, for example, describes a method for preparing E/Z-homofarnesylic acid by carbonylation of (E)-nerolidol with addition of catalytic amounts of palladium(II) chloride. E/Z-Homofarnesylic acid is obtained as an isomeric mixture.

WO 2018/153727 describes a method for preparing 3-unsaturated carboxylic acids by carbonylation of the corresponding allylic alcohols or acylated alcohols, for example the carbonylation of (E)-nerolidol in the presence of a transition metal catalyst and in the presence of an anhydride of an organic acid at a temperature of at most 100° C. An E/Z isomeric mixture is generally obtained in this case which, in addition to the 3-(E)-isomer, also comprises the 3-(Z)-isomer in significant amounts, for example an isomeric mixture of (3E,7E)-homofarnesylic acid and (3Z,7E)-homofarnesylic acid generally in a ratio from 50:50 to 70:30. Separation of the respective isomeric mixtures is possible chromatographically or by distillation only with great effort.

WO 2018/154048 describes a first method for the partial separation of stereochemically pure (3E,7E)-homofarnesylic acid, using certain lipases and alcohols, from compositions comprising (3Z,7E)-homofarnesylic acid and (3E,7E)-homofarnesylic acid. Compositions are obtained in the first method comprising an increased content of (3Z,7E)-homofarnesylic acid and reduced content of (3E,7E)-homofarnesylic acid compared to the starting composition. A second method is also described for the partial separation of stereochemically pure (3E,7E)-homofarnesylic acid, using certain lipases and water, from compositions comprising (3Z, 7E)-homofarnesylic acid ester and (3E,7E)-homofarnesylic acid ester. Compositions are obtained in the second method comprising an increased content of (3Z,7E)-homofarnesylic acid ester and reduced content of (3E,7E)-homofarnesylic acid ester compared to the starting composition. The homofarnesylic acid ester mixtures thus obtained can then be converted by ester cleavage (acid-catalyzed, base-catalyzed or enzyme-catalyzed) to mixtures of (3E,7E)- and (3Z,7E)-homofarnesylic acid. In the isolation of (3E,7E)-homofarnesylic acid by both methods, significant amounts of (3Z,7E)-homofarnesylic acid are therefore obtained, which cannot be used for preparing (−)-ambrox.

For an economically viable procedure, it is desirable that the undesired product present in the compositions from the prior art, i.e. the 3-(Z)-isomer, can be at least partially converted to the 3-(E)-isomer, in order to increase the fraction of product of value, i.e. of (3E,7E)-homofarnesylic acid.

In principle, methods for isomerizing (Z)-alkenes to (E)-alkenes are known. Possible and known are thermal conversions, photochemical conversions, conversions using catalysts and conversions mediated by reagents.

M. Yus and F. Foubelo in Science of Synthesis, 47 (2009), p. 1076 describe various methods for isomerizing Z-alkenes to the thermodynamically more stable (E)-alkenes, for example in the presence of a transition metal catalyst such as trihydrido(triphos) rhodium (III). The conversions are possible, in part, even below 100° C.

Jung et al. in J. Org. Chem. 2007, 72, 5424-5426 describe an isomerization method in which a palladium catalyst and over-stoichiometric amounts of tributyltin hydride are required.

Owing to the high temperatures, purely thermal conversions of (Z)-alkenes are usually not economically viable alternatives since most (Z)-alkenes are configuration stable at temperatures below 180° C. Thermal isomerization therefore in most cases requires temperatures above 180° C., as described in J. Org. Chem. 1987, 52, pages 5636-5638.

However, no procedure is found in the literature for thermal Z/E isomerization which proceeds effectively and economically under mild reaction conditions. It is to be understood here that the isomerization does not proceed photochemically but thermally at temperatures below 180° C. and in the absence of a transition metal catalyst.

The methods known from the prior art are only very generally suitable for isomerizing double bonds but in some cases with shifting of the double bond(s). For example, catalysts, that lead to the shift of double bonds, are described by C. Mazet et al. in Acc. Chem. Res. 2016, 49, p. 1232 or in JACS 2014, 136, p. 16882.

A need therefore exists for a method which under mild reaction conditions converts a 3-(Z)-unsaturated carboxylic acid to a 3-(E)-unsaturated carboxylic acid. In particular, the method should be able to convert (3Z,7E)-homofarnesylic acid selectively to (3E,7E)-homofarnesylic acid, without isomerizing the other double bonds. The conversion should take place efficiently and in one synthetic step.

The object of the present invention therefore is the provision of a method for isomerizing a 3-(Z)-unsaturated carboxylic acid to a 3-(E)-unsaturated carboxylic acid under mild reaction conditions. In particular, the method is intended to convert (3Z,7E)-4,8,12-trimethyltrideca-3,7,11-trienoic acid or a salt thereof to (3E,7E)-4,8,12-trimethyltrideca-3,7,11-trienoic acid or a salt thereof under mild reaction conditions.

It has now been found that, surprisingly, a 3-(Z)-unsaturated carboxylic acid is isomerized at least partially to the 3-(E)-unsaturated carboxylic acid in the presence of a base and an acylating agent such as an anhydride of an organic acid or a ketene compound. It has also been found that the isomerization can be carried out at temperatures below 180° C. and in the absence of a transition metal catalyst.

SUMMARY OF THE INVENTION

The subject of the invention is a method for isomerizing a 3-(Z)-unsaturated carboxylic acid of the formula I-Z

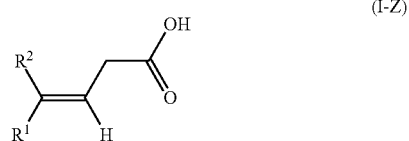

(I-Z)

or a salt thereof,
in which
R¹ is hydrogen, linear or branched $C_1$-$C_{24}$-alkyl, linear or branched $C_2$-$C_{24}$-alkenyl having 1, 2, 3 or more than 3 C—C double bonds, $C_5$-$C_{12}$-cycloalkyl that is unsubstituted or substituted by 1, 2 or 3 $C_1$-$C_6$-alkyl radicals, or $C_6$-$C_{20}$-aryl that is unsubstituted or substituted by 1, 2 or 3 $C_1$-$C_6$-alkyl radicals;
and
R² is linear or branched $C_1$-$C_{24}$-alkyl, linear or branched $C_2$-$C_{24}$-alkenyl having 1, 2, 3 or more than 3 C—C double bonds, $C_5$-$C_{12}$-cycloalkyl that is unsubstituted or substituted by 1, 2 or 3 $C_1$-$C_6$-alkyl radicals, or $C_6$-$C_{20}$-aryl that is unsubstituted or substituted by 1, 2 or 3 $C_1$-$C_6$-alkyl radicals;
with the proviso that R² has a higher priority than R¹ in accordance with IUPAC;

to give a 3-(E)-unsaturated carboxylic acid of the formula I-E

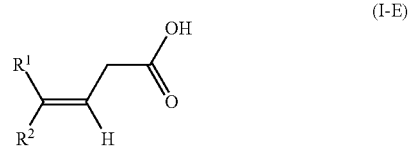

(I-E)

or a salt thereof;
wherein the isomerization of the compound of the formula I-Z or a salt thereof is effected in the presence of an anhydride of an organic acid and a base;
or
wherein the isomerization of the compound of the formula I-Z or a salt thereof is effected in the presence of a base and a ketene of the formula V

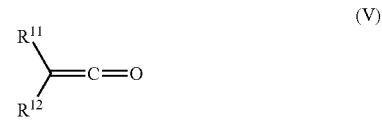

(V)

wherein
R¹¹ and R¹², independently of each other, are selected from hydrogen, linear or branched $C_1$-$C_{24}$-alkyl, $C_5$-$C_{12}$-cycloalkyl that is unsubstituted or substituted by 1, 2 or 3 $C_1$-$C_6$-alkyl radicals, or $C_6$-$C_{14}$-aryl that is unsubstituted or substituted by 1, 2 or 3 $C_1$-$C_6$-alkyl radicals.

In a specific embodiment, the subject matter of the invention is a method for isomerizing a 3-(Z)-unsaturated carboxylic acid of the formula I-Z

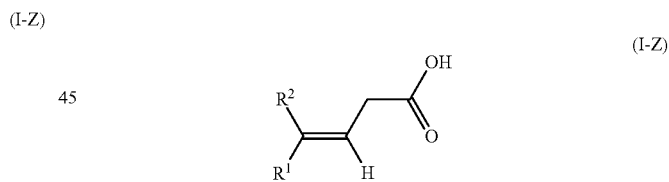

(I-Z)

or a salt thereof,
in which
R¹ is hydrogen, linear or branched $C_1$-$C_{24}$-alkyl, linear or branched $C_2$-$C_{24}$-alkenyl having 1, 2, 3 or more than 3 C—C double bonds, $C_5$-$C_{12}$-cycloalkyl that is unsubstituted or substituted by 1, 2 or 3 $C_1$-$C_6$-alkyl radicals, or $C_6$-$C_{20}$-aryl that is unsubstituted or substituted by 1, 2 or 3 $C_1$-$C_6$-alkyl radicals;
R² is linear or branched $C_1$-$C_{24}$-alkyl, linear or branched $C_2$-$C_{24}$-alkenyl having 1, 2, 3 or more than 3 C—C double bonds, $C_5$-$C_{12}$-cycloalkyl that is unsubstituted or substituted by 1, 2 or 3 $C_1$-$C_6$-alkyl radicals, or $C_6$-$C_{20}$-aryl that is unsubstituted or substituted by 1, 2 or 3 $C_1$-$C_6$-alkyl radicals;
with the proviso that R² has a higher priority than R¹ in accordance with IUPAC;

to give a 3-(E)-unsaturated carboxylic acid of the formula I-E

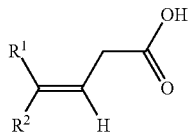

(I-E)

or a salt thereof;
wherein the isomerization of the compound of the formula I-Z or a salt thereof is effected in the presence of an anhydride of an organic acid and a base.

DESCRIPTION OF THE INVENTION

In the general formulae of the compounds I-Z and I-E

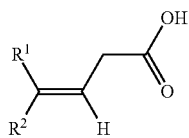

(I-Z)

(I-E)

it is self-evident that E- and Z-isomers can only be present if two different substituents $R^1$ and $R^2$ are bonded to the double bond. In the context of the present invention, the substituent $R^2$ has a higher priority in accordance with IUPAC (International Union of Pure and Applied Chemistry). According to IUPAC, the substituents are prioritized in sequence in accordance with the Cahn-Ingold-Prelog rule (see E/Z notation, https://en.wikipedia.org/wiki/E-Z_notation).

In the compounds of the general formulae (I), (II.2), (III.2) and (IV.2)

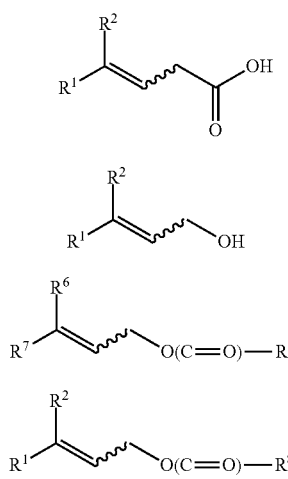

(I)

(II.2)

(III.2)

(IV.2)

the wavy bond is intended to indicate that it can take the form in each case of the pure Z-isomer, the pure E-isomer or any desired E/Z-mixture.

The method according to the invention enables the at least partial isomerization of the 3-(Z)-unsaturated carboxylic acid of the formula I-Z or salt thereof to the 3-(E)-unsaturated carboxylic acid or salt thereof under mild reaction conditions.

In the context of the present invention, the expression "aliphatic" comprises hydrocarbon radicals in which the carbon atoms are arranged in straight or branched chains.

In the context of the present invention, the expression "cycloaliphatic" comprises cyclic saturated or unsaturated carbon radicals, excluding aromatic radicals.

In the context of the present invention, the expression "alkyl", and also all alkyl parts in alkoxy, alkylamino and dialkylamino, comprise saturated, linear or branched hydrocarbon radicals having 1 to 4 ("$C_1$-$C_4$-alkyl"), 1 to 6 ("$C_1$-$C_6$-alkyl"), 1 to 10 ("$C_1$-$C_{10}$-alkyl"), 1 to 20 ("$C_1$-$C_{20}$-alkyl") or 1 to 24 ("$C_1$-$C_{24}$-alkyl") carbon atoms. Examples of linear or branched $C_1$-$C_4$-alkyl are methyl, ethyl, n-propyl, 1-methylethyl, n-butyl, 1-methylpropyl, 2-methylpropyl, 1,1-dimethylethyl. Examples of linear or branched $C_1$-$C_6$-alkyl, in addition to the definitions mentioned for $C_1$-$C_4$-alkyl, are n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. Examples of linear or branched $C_1$-$C_{10}$-alkyl, in addition to the definitions mentioned for $C_1$-$C_6$-alkyl, are heptyl, octyl, nonyl, decyl and positional isomers thereof. Examples of $C_1$-$C_{20}$-alkyl, in addition to the definitions mentioned for $C_1$-$C_{10}$-alkyl, are undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, eicosyl and positional isomers thereof.

In the context of the present invention, the expression "alkenyl" comprises unsaturated, linear or branched hydrocarbon radicals having 2 to 4 ($C_2$-$C_4$-alkenyl), up to 6, to 8, to 10, to 16, to 20 or up to 24 carbon atoms and one, two, three or more than three double bonds in any position. Examples of linear or branched $C_2$-$C_{24}$-alkenyl having one double bond are vinyl, allyl (2-propen-1-yl), 1-methylprop-2-en-1-yl, 2-buten-1-yl, 3-buten-1-yl, n-pentenyl, n-hexenyl, n-heptenyl, n-octenyl, n-nonenyl, n-decenyl, n-undecenyl, n-dodecenyl, n-tridecenyl, n-tetradecenyl, n-pentadecenyl, n-hexadecenyl, n-heptadecenyl, n-octadecenyl, oleyl, n-nonadecenyl, n-eicosenyl, n-heneicosenyl, n-docosenyl, n-tricosenyl, n-tetracosenyl and constitutional isomers thereof. Examples of linear or branched $C_4$-$C_{24}$-alkenyl having two or three double bonds in any position are n-butadienyl, n-pentadienyl, n-hexadienyl, n-heptadienyl, n-octadienyl, n-octatrienyl, n-nonadienyl, n-nonatrienyl, n-decadienyl, n-decatrienyl, n-undecadienyl, n-undecatrienyl, n-dodecadienyl, n-dodecatrienyl, n-tridecadienyl, n-tridecatrienyl, n-tetradecadienyl, n-tetradecatrienyl, n-pentadecadienyl, n-pentadecatrienyl, n-hexadecadienyl, n-hexadecatrienyl, n-heptadecadienyl, n-heptadecatrienyl, n-octadecadienyl, n-octadecatrienyl, n-nonadecadienyl, n-nonadecatrienyl, n-eicosadienyl, n-eicosatrienyl, n-heneicosadienyl, n-heneicosatrienyl, n-docosadienyl, n-docosatrienyl, n-tricosadienyl, n-tricosatrienyl, n-tetracosadienyl, n-tetracosatrienyl, linolenyl and constitutional isomers thereof. Any double bond in $C_2$-$C_{24}$-alkenyl can each be present (unless stated otherwise) independently of one another in the E and in the Z configuration.

In the context of the present invention, the expression "cycloalkyl" comprises monocyclic, saturated hydrocarbon radicals having 3 to 8 ("$C_3$-$C_8$-cycloalkyl"), preferably 5 to 7 carbon ring members ("$C_5$-$C_7$-cycloalkyl"). Examples of $C_3$-$C_8$-cycloalkyl are cyclopropyl, cyclobutyl, cyclopentyl, cyclohexyl, cycloheptyl and cyclooctyl.

In the context of the present invention, the expression "heterocyclyl" (also referred to as heterocycloalkyl) comprises monocyclic, saturated cycloaliphatic groups having in general 5 to 8 ring atoms, preferably 5 or 6 ring atoms, in which 1 or 2 of the ring carbon atoms have been replaced by heteroatoms or heteroatom-containing groups selected from oxygen, nitrogen, NH and N($C_1$-$C_4$-alkyl). Examples of such heterocycloaliphatic groups are pyrrolidinyl, piperidinyl, tetrahydrofuranyl and tetrahydropyranyl.

In the context of the present invention, the expression "aryl" comprises a mononuclear, binuclear or trinuclear aromatic ring system comprising 6 to 20 carbon ring members. Examples of unsubstituted $C_6$ to -$C_{10}$-aryl are phenyl and naphthyl. Examples of $C_6$-$C_{14}$-aryl are phenyl, naphthyl, anthracenyl and phenanthrenyl. Substituted aryl groups bear in general 1, 2, 3, 4 or 5, preferably 1, 2 or 3, identical or different substituents. Suitable substituents are selected in particular from alkyl, cycloalkyl, aryl, alkoxy, dialkylamino. Examples of aryl bearing 1, 2 or 3 substituents selected from $C_1$-$C_6$-alkyl are tolyl, xylyl and mesityl.

In the context of the present invention, the expression "hetaryl" comprises a five- to six-membered aromatic heteromonocycle comprising one, two, three or four heteroatoms from the group of oxygen, nitrogen or sulfur, and 9- or 10-membered aromatic heterobicylces, e.g. C-bonded 5-membered heteroaryl, comprising one to three nitrogen atoms or one or two nitrogen atoms and one sulfur or oxygen atom as ring members, such as furyl, thienyl, pyrrolyl, isoxazolyl, isothiazolyl, pyrazolyl, oxazolyl, thiazolyl, imidazolyl, 4-imidazolyl, 1,2,4-oxadiazolyl, 1,2,4-thiadiazolyl, 1,2,4-triazolyl, 1,3,4-oxadiazolyl; 5-membered heteroaryl bonded via nitrogen, comprising one to three nitrogen atoms as ring members, such as pyrrol-1-yl, pyrazol-1-yl, imidazol-1-yl, 1,2,3-triazol-1-yl and 1,2,4-triazol-1-yl; 6-membered heteroaryl, comprising one to three nitrogen atoms as ring members, such as pyridinyl, pyridazinyl, pyrimidinyl, pyrazinyl, 1,3,5-triazinyl and 1,2,4-triazinyl.

Halogen is fluorine, chlorine, bromine or iodine. Halide is fluoride, chloride, bromide or iodide.

Alkali metals correspond to the group 1 elements of the Periodic Table of the Elements in accordance with IUPAC, for example lithium, sodium, potassium, rubidium or cesium, preferably lithium, sodium or potassium, especially sodium or potassium.

Alkaline earth metals correspond to the group 2 elements of the Periodic Table of the Elements in accordance with IUPAC, for example beryllium, magnesium, calcium, strontium or barium, preferably magnesium or calcium.

Group 8 of the Periodic Table of the Elements in accordance with IUPAC comprises, inter alia, iron, ruthenium and osmium. Group 9 of the Periodic Table of the Elements in accordance with IUPAC comprises, inter alia, cobalt, rhodium, iridium. Group 10 of the Periodic Table of the Elements in accordance with IUPAC comprises, inter alia, nickel, palladium and platinum.

In the context of the present invention, the expression "salts thereof" means salts of carboxyl groups. Salts of carboxyl groups can be produced in a known way and comprise inorganic salts, for example sodium, potassium, calcium, ammonium, etc., salts with organic bases, for example amines and salts of acid addition, for example salts with inorganic acids, such as hydrochloric acid or sulfuric acid and salts with organic acids, such as acetic acid.

In the context of the present invention, the expression "ammonium salts" comprises both salts derived from $NH_4^+$ and mono-, di-, tri- and tetraorganylammonium salts. The radicals bonded to the ammonium nitrogen are generally in each case independently selected from hydrogen and aliphatic, alicyclic and aromatic hydrocarbon groups. Preferably, the radicals bonded to the ammonium nitrogen are each independently selected from hydrogen and aliphatic radicals, especially selected from hydrogen and $C_1$-$C_{20}$-alkyl.

In the context of the present invention, the expression "acyl" comprises alkanoyl or aroyl groups having in general 1 to 11, preferably 2 to 8 carbon atoms, for example, the formyl, acetyl, propionyl, butyryl, pentanoyl, benzoyl or naphthoyl group.

"Stereoisomers" are compounds of identical constitution but different atom arrangement in three-dimensional space.

"Enantiomers" are stereoisomers which behave as mirror images to one another. "Enantiomerically pure" signifies that, besides the enantiomer specifically named, no further enantiomeric form of a chemical compound having at least one asymmetric center is detectable analytically.

In the context of the present invention, the term "terpene-like hydrocarbon radicals" comprises hydrocarbon radicals derived formally from one, two, three or more than three isoprene units. The terpene-like hydrocarbon radicals may in this case still comprise double bonds or be fully saturated. The double bonds in this case may take up any positions, wherein cumulated double bonds are excluded.

In the context of the present invention, the term "farnesol (3,7,11-trimethyl-2,6,10-dodecatrien-1-ol)" comprises the (2E),(6E)-isomer, (2Z),(6Z)-isomer, (2Z),(6E)-isomer and the (2E),(6Z)-isomer and also mixtures of two, three or all of the isomers of farnesol mentioned. Farnesol is commercially available.

Nerolidol has one chiral center and can exist as an E/Z mixture and thus there are four stereoisomers. In the context of the present invention, the term "nerolidol (3,7,11-trimethyl-1,6,10-dodecatrien-3-ol)" comprises the (3S),(6Z)-isomer, (3R),(6Z)-isomer, (3S),(6E)-isomer, (3R),(6E)-isomer and any desired mixtures thereof. Nerolidol is commercially available. Nerolidyl acetate (3,7,11-trimethyl-1,6,10-octatrienyl acetate) is the acetylation product of nerolidol. It is commercially available.

Another name for homofarnesylic acid is 4,8,12,-trimethyltrideca-3,7,11-trienoic acid. Another name for (3Z,7E)-homofarnesylic acid is therefore (3Z,7E)-4,8,12-trimethyltrideca-3,7,11-trienoic acid. Another name for (3E,7E)-homofarnesylic acid is therefore (3E,7E)-4,8,12-trimethyltrideca-3,7,11-trienoic acid.

The suitable and preferred conditions stated below for the method according to the invention apply to the isomerization in the presence of a base and an anhydride of an organic acid as well as to the isomerization in the presence of a base and a ketene compound of formula V, unless otherwise stated.

The following embodiments apply both to the use of the pure (Z)-isomer, a composition comprising the (Z)-isomer, and to the use of a composition comprising the (E)-isomer and the (Z)-isomer, unless stated to the contrary.

In the compounds of the formulae I-Z and I-E, $R^1$ is preferably hydrogen, linear or branched $C_1$-$C_{16}$-alkyl or linear or branched $C_2$-$C_{16}$-alkenyl having one or two non-conjugated double bonds. $R^1$ is particularly hydrogen or $C_1$-$C_4$-alkyl, especially $C_1$-$C_2$-alkyl. In the compounds of the formulae I-Z and I-E, $R^2$ is preferably linear or branched $C_1$-$C_{16}$-alkyl or linear or branched $C_2$-$C_{16}$-alkenyl having one or two non-conjugated double bonds, especially a terpene-like hydrocarbon radical. $R^2$ is particularly linear or branched $C_6$-$C_{16}$-alkyl or linear or branched $C_6$-$C_{16}$-alkenyl having one or two non-conjugated double bonds. $R^2$ preferably has one carbon atom more than $R^1$.

Suitable as 3-(Z)-unsaturated carboxylic acid of the formula I-Z is the pure 3-(Z)-unsaturated carboxylic acid; compositions comprising the 3-(Z)-unsaturated carboxylic acid; and compositions comprising the 3-(Z)-unsaturated carboxylic acid and the 3-(E)-unsaturated carboxylic acid. In a preferred embodiment, the proportion of 3-(Z)-unsaturated carboxylic acid in the composition provided is higher than the proportion of 3-(E)-unsaturated carboxylic acid.

According to a first embodiment of the present invention, the pure isomer of the formula I-Z or a salt thereof is used in the method according to the invention.

According to a further preferred embodiment of the present invention, a composition is used in the method according to the invention comprising the compound of the formula I-Z or a salt thereof and the compound of the formula I-E or a salt thereof. The method according to the invention gives rise to a composition in which the content of compound of the formula I-E is increased compared to the content of compound I-E in the composition used.

Preferably, in the composition used, the ratio by weight of compound I-Z or salt thereof to compound I-E or salt thereof is greater than 50:50, preferably greater than 85:15.

The method according to the invention is particularly suitable for increasing the content of (3E,7E)-4,8,12-trimethyltrideca-3,7,11-trienoic acid or a salt thereof in a composition comprising (3Z,7E)-4,8,12-trimethyltrideca-3,7,11-trienoic acid as compound of the formula I-Z and (3E,7E)-4,8,12-trimethyltrideca-3,7,11-trienoic acid as compound of the formula I-E.

Compositions comprising E/Z mixtures of a 3-unsaturated carboxylic acid or salt thereof, specifically (3E,7E)-4,8,12-trimethyltrideca-3,7,11-trienoic acid or salt thereof and (3Z,7E)-4,8,12-trimethyltrideca-3,7,11-trienoic acid or salt thereof, are obtained, for example, by the method described in WO 2018/153727. According to a first embodiment (variant 1) for preparing compositions comprising at least one E/Z mixture of an unsaturated carboxylic acid of the general formula I

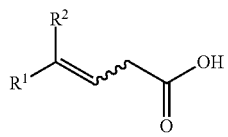
(I)

or a salt thereof, where $R^1$ and $R^2$ are as defined above, an allyl alcohol, selected from compounds of the general formulae (II.1) and (II.2),

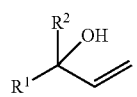
(II.1)

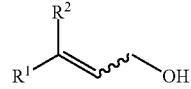
(II.2)

is subjected to a carbonylation by reaction with carbon monoxide in the presence of a transition metal catalyst comprising at least one metal from groups 8, 9 or 10 of the Periodic Table of the Elements, wherein the reaction is effected additionally in the presence of at least one organophosphorus compound as ligand and in the presence of a substoichiometric amount, based on the allyl alcohol, of a compound A), which is selected from anhydrides of aliphatic $C_1$-$C_{12}$-monocarboxylic acids, anhydrides of aliphatic $C_4$-$C_{20}$-dicarboxylic acids, anhydrides of cycloaliphatic $C_7$-$C_{20}$-dicarboxylic acids, anhydrides of aromatic $C_8$-$C_{20}$-dicarboxylic acids and acylated allyl alcohols of the formulae (III.1) and (III.2)

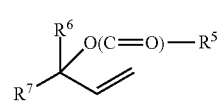
(III.1)

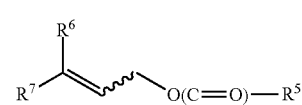
(III.2)

in which
$R^5$ is $C_1$-$C_5$-alkyl; and
$R^6$ and $R^7$ have one of the definitions specified for $R^1$ and $R^2$;
and wherein the reaction is conducted at a temperature of at most 100° C.

According to a second embodiment (variant 2) for preparing a composition comprising at least one E/Z mixture of an unsaturated carboxylic acid of the general formula (I)

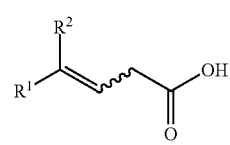
(I)

or a salt thereof,
where $R^1$ and $R^2$ are as defined above,
an acylated alcohol, selected from compounds of the general formulae (IV.1) and (IV.2)

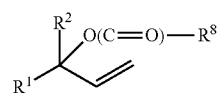
(IV.1)

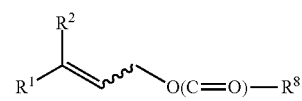
(IV.2)

where $R^8$ is $C_1$-$C_5$-alkyl, is subjected to a carbonylation by reaction with carbon monoxide in the presence of a transition metal catalyst comprising at least one metal from groups 8, 9 or 10 of the Periodic Table of the Elements, wherein the reaction is effected additionally in the presence of at least one organophosphorus compound as ligand and in the presence of water and wherein the reaction is conducted at a temperature of at most 100° C.

According to a third embodiment (variant 3) for preparing a composition comprising at least one E/Z mixture of an unsaturated carboxylic acid of the general formula (I)

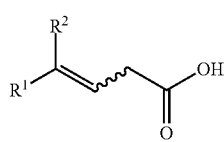

(I)

or a salt thereof, where $R^1$ and $R^2$ are as defined above, an allyl alcohol, selected from compounds of the general formulae (II.1) and (II.2),

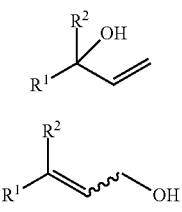

(II.1)

(II.2)

is subjected to a carbonylation by reaction with carbon monoxide in the presence of a transition metal catalyst comprising at least one metal from groups 8, 9 or 10 of the Periodic Table of the Elements, wherein the reaction is effected additionally in the presence of at least one organophosphorus compound as ligand and in the presence of a substoichiometric amount, based on the allyl alcohol, of a compound B)

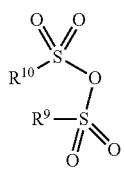

(B)

in which
$R^9$ and $R^{10}$ are each independently $C_1$-$C_6$-alkyl, $C_1$-$C_6$-fluoroalkyl or phenyl, which is unsubstituted or has been substituted by one substituent selected from bromine, nitro and $C_1$-$C_4$-alkyl;
and wherein the reaction is conducted at a temperature of at most 100° C.

The carbonylation is carried out according to the three variants mentioned above in the presence of a transition metal catalyst comprising at least one metal from groups 8, 9 or 10 of the Periodic Table of the Elements. The transition metals used are preferably palladium, ruthenium, rhodium, iridium and iron, particularly preferably palladium. Monodentate and bidentate phosphorus ligands are suitable as organophosphorus compounds. In principle, it does not matter which type of organophosphorus compound is used and therefore it is generally possible to use cost-effective tertiary monodentate phosphines. In addition, the carbonylation catalysts used can have at least one further ligand.

It may be appropriate to carry out the carbonylation according to previously stated variants 1 and 3 in the presence of a nucleophilic reagent. Examples of nucleophilic reagents are 4-($C_1$-$C_4$-alkyl)pyridine, 4-(1-pyrrolidinyl)pyridine and 4-(di-($C_1$-$C_4$-alkyl)amino)pyridine. The carbonylation can be carried out according to all variants mentioned above in the presence or absence of a base, which is different from the nucleophilic reagent. However, the carbonylation is preferably carried out in the presence of a base. Suitable bases are organic and inorganic bases. Suitable bases are especially amines. It is also advantageous to carry out the carbonylation with exclusion of, or reduced content of, atmospheric oxygen. The carbonylation can be carried out in accordance with all previously stated variants over a wide pressure range such as from atmospheric pressure to at most 90 bar, preferably up to at most 30 bar, preferably up to at most 25 bar, more preferably at most 20 bar and especially at most 15 bar. Suitable pressure ranges are, for example, 1.1 to 90 bar, 1.1 to 30 bar, 2 to 20 bar, 5 to 15 bar. The reaction temperature according to the variants described above can be selected over a wide range from room temperature (20° C.) to 100° C., but which is preferably at most 80° C., especially not exceeding 75° C. The reaction output of the carbonylation can be worked-up by distillation. After distillation, compositions are obtained comprising (3E,7E)-4,8,12-trimethyltrideca-3,7,11-trienoic acid, (3Z,7E)-4,8,12-trimethyltrideca-3,7,11-trienoic acid and also low amounts of (2E,7E)-4,8,12-trimethyltrideca-3,7,11-trienoic acid and possibly further compounds.

The methods specified above enable the preparation of (3E,7E)- and (3Z,7E)-4,8,12-trimethyltrideca-3,7,11-trienoic acid or salt thereof, starting from commercially available substances such as farnesol or nerolidol, under mild reaction conditions in high yield. In particular, the methods specified above enable the preparation of compositions comprising (3E,7E)-4,8,12-trimethyltrideca-3,7,11-trienoic acid or salt thereof and (3Z,7E)-4,8,12-trimethyltrideca-3,7,11-trienoic acid or salt thereof in a ratio by weight generally from 80:20 to 50:50, preferably from 70:30 to 50:50, starting from (E)-nerolidol. The proportion of (3E,7E)-4,8,12-trimethyltrideca-3,7,11-trienoic acid in the resulting isomeric mixture is generally higher than the proportion of (3Z,7E)-4,8,12-trimethyltrideca-3,7,11-trienoic acid. The resulting composition can be subjected to an at least partial enrichment of one isomer by isomer separation as described below or also by distillation for example.

A possible isomer separation of a mixture initially obtained comprising a 3-(Z)-unsaturated carboxylic acid and a 3-(E)-unsaturated carboxylic acid is described in WO 2018/154048. In particular, WO 2018/154048 describes an isomer separation of a mixture comprising (3E,7E)- and (3Z,7E)-4,8,12-trimethyltrideca-3,7,11-trienoic acid, to obtain a first stream enriched in (3E,7E)-4,8,12-trimethyltrideca-3,7,11-trienoic acid and to obtain a second stream enriched in (3Z,7E)-4,8,12-trimethyltrideca-3,7,11-trienoic acid.

Enzymatically catalyzed esterifications starting from a 3-(Z)-unsaturated carboxylic acid and a 3-(E)-unsaturated carboxylic acid enable the preparation of compositions comprising a 3-(Z)-unsaturated carboxylic acid and a 3-(E)- unsaturated carboxylic acid, wherein the proportion of 3-(Z)-unsaturated carboxylic acid is higher than the proportion of 3-(E)-unsaturated carboxylic acid. Such compositions are obtained, for example, in the methods of WO 2018/154048.

In the method according to the invention, a composition is preferably used comprising (3Z,7E)-4,8,12-trimethyltrideca-3,7,11-trienoic acid as compound of the formula I-Z and (3E,7E)-4,8,12-trimethyltrideca-3,7,11-trienoic acid as compound of the formula I-E and which is obtained by a method in which
- (a) a first composition is provided comprising (3Z,7E)-4,8,12-trimethyltrideca-3,7,11-trienoic acid and (3E,7E)-4,8,12-trimethyltrideca-3,7,11-trienoic acid;
- (b) the first composition from step (a) is subjected to an enzyme-catalyzed esterification in the presence of an alcohol and a lipase enzyme, wherein a composition is obtained comprising (3E,7E)-4,8,12-trimethyltrideca-3,7,11-trienoic acid ester, unreacted (3E,7E)-4,8,12-trimethyltrideca-3,7,11-trienoic acid and unreacted (3Z,7E)-4,8,12-trimethyltrideca-3,7,11-trienoic acid; and
- (c) from the composition obtained in step (b), a composition comprising (3E,7E)-4,8,12-trimethyltrideca-3,7,11-trienoic acid ester is separated off and a second composition is obtained comprising (3Z,7E)-4,8,12-trimethyltrideca-3,7,11-trienoic acid and (3E,7E)-4,8,12-trimethyltrideca-3,7,11-trienoic acid, wherein the content of (3Z,7E)-4,8,12-trimethyltrideca-3,7,11-trienoic acid in the second composition is increased compared to the first composition provided in step (a).

Examples of suitable lipases in step (b) are *Candida antarctica* lipase (CALB) and a form immobilized on a polymeric support such as Novozym 435®. The enzyme-catalyzed esterification is carried out preferably in the presence of an aliphatic alcohol. Suitable aliphatic alcohols are $C_1$-$C_{20}$-alkanols such as methanol, ethanol, n-propanol, isopropanol, n-butanol, isobutanol, sec-butanol, n-pentanol, n-hexanol, n-heptanol and n-octanol. The enzyme-catalyzed esterification can be carried out optionally in the presence of a diluent or solvent. Examples of suitable diluents or solvents are particularly aliphatic hydrocarbons such as hexane, cyclohexane, heptane, octane; aromatic hydrocarbons such as toluene, xylene; dialkyl ethers such as methyl tert-butyl ether and diisopropyl ether. Typically, 1-5 equivalents of alcohol are used per equivalent of (3E,7E)-4,8,12-trimethyltrideca-3,7,11-trienoic acid. The esterification is typically carried out at a temperature in a range from 0 to 80° C.

The lipase esterifies the 3E,7E-isomer with alcohols very much faster than the corresponding 3Z,7E-isomer resulting in a separable composition comprising (3E,7E)-4,8,12-trimethyltrideca-3,7,11-trienoic acid ester, (3Z,7E)-4,8,12-trimethyltrideca-3,7,11-trienoic acid and (3E,7E)-4,8,12-trimethyltrideca-3,7,11-trienoic acid.

The composition obtained in step (b) can be separated by extraction or distillation, wherein a composition comprising (3E,7E)-4,8,12-trimethyltrideca-3,7,11-trienoic acid ester is separated off and a second composition is obtained comprising (3Z,7E)-4,8,12-trimethyltrideca-3,7,11-trienoic acid and (3E,7E)-4,8,12-trimethyltrideca-3,7,11-trienoic acid, wherein the content of (3Z,7E)-4,8,12-trimethyltrideca-3,7,11-trienoic acid in the second composition is increased compared to the first composition provided in step (a).

Enzymatically catalyzed saponifications, starting from compositions comprising a 3-(Z)-unsaturated carboxylic acid ester and a 3-(E)-unsaturated carboxylic acid ester, likewise enable the preparation of compositions comprising a 3-(Z)-unsaturated carboxylic acid and a 3-(E)-unsaturated carboxylic acid, wherein the proportion of 3-(Z)-unsaturated carboxylic acid is higher than the proportion of 3-(E)-unsaturated carboxylic acid. Such compositions are obtained, for example, in the methods of WO 2018/154048.

Therefore, in the method according to the invention, a composition is likewise preferably used comprising (3Z,7E)-4,8,12-trimethyltrideca-3,7,11-trienoic acid as compound of the formula I-Z and (3E,7E)-4,8,12-trimethyltrideca-3,7,11-trienoic acid as compound of the formula I-E and which is obtained by a method in which
- (d) a composition is provided comprising (3E,7E)-4,8,12-trimethyltrideca-3,7,11-trienoic acid ester and (3Z,7E)-4,8,12-trimethyltrideca-3,7,11-trienoic acid ester;
- (e) the composition provided in step (d) is subjected to an enzyme-catalyzed ester cleavage in the presence of a lipase enzyme, wherein a composition is obtained comprising (3E,7E)-4,8,12-trimethyltrideca-3,7,11-trienoic acid, unreacted (3E,7E)-4,8,12-trimethyltrideca-3,7,11-trienoic acid ester and unreacted (3Z,7E)-4,8,12-trimethyltrideca-3,7,11-trienoic acid ester;
- (f) from the composition obtained in step (e), a composition is separated off comprising (3E,7E)-4,8,12-trimethyltrideca-3,7,11-trienoic acid and a composition is obtained comprising (3Z,7E)-4,8,12-trimethyltrideca-3,7,11-trienoic acid ester and (3E,7E)-4,8,12-trimethyltrideca-3,7,11-trienoic acid ester; and
- (g) the composition obtained in step (f), comprising (3Z,7E)-4,8,12-trimethyltrideca-3,7,11-trienoic acid ester and (3E,7E)-4,8,12-trimethyltrideca-3,7,11-trienoic acid ester, is subjected to an ester cleavage to obtain a composition comprising (3Z,7E)-4,8,12-trimethyltrideca-3,7,11-trienoic acid or a salt thereof and (3E,7E)-4,8,12-trimethyltrideca-3,7,11-trienoic acid or a salt thereof.

The composition provided in step (d) can be obtained by esterifying (3E,7E)-4,8,12-trimethyltrideca-3,7,11-trienoic acid and (3Z,7E)-4,8,12-trimethyltrideca-3,7,11-trienoic acid with an alcohol.

The composition provided in step (d) is subjected in step (e) to an enzyme-catalyzed ester cleavage in the presence of a lipase enzyme, wherein a composition is obtained comprising (3E,7E)-4,8,12-trimethyltrideca-3,7,11-trienoic acid, unreacted (3E,7E)-4,8,12-trimethyltrideca-3,7,11-trienoic acid ester and unreacted (3Z,7E)-4,8,12-trimethyltrideca-3,7,11-trienoic acid ester. Examples of suitable lipases are *Candida antarctica* lipase (CALB) and a form immobilized on a polymeric support such as Novozym 435®. The enzyme-catalyzed ester cleavage is typically effected in the presence of water.

The composition obtained in step (e) can be separated by distillation or extraction. From the composition obtained in step (e), a composition is therefore separated off in step (f) comprising (3E,7E)-4,8,12-trimethyltrideca-3,7,11-trienoic acid and a composition is obtained comprising (3Z,7E)-4,8,12-trimethyltrideca-3,7,11-trienoic acid ester and (3E,7E)-4,8,12-trimethyltrideca-3,7,11-trienoic acid ester.

The ester cleavage in step (g) can be acid-, base- or enzyme-catalyzed, wherein a composition is obtained comprising (3Z,7E)-4,8,12-trimethyltrideca-3,7,11-trienoic acid or a salt thereof and (3E,7E)-4,8,12-trimethyltrideca-3,7,11-trienoic acid or a salt thereof.

The composition used in the method according to the invention preferably comprises (3E,7E)-4,8,12-trimethyltrideca-3,7,11-trienoic acid or a salt thereof and (3Z,7E)-4,8,12-trimethyltrideca-3,7,11-trienoic acid or a salt thereof in a ratio by weight from 1:99 to 50:50. In particular, a composition is used in the method according to the invention in which the ratio by weight of (3E,7E)-4,8,12-trimethyltrideca-3,7,11-trienoic acid or a salt thereof to (3Z,7E)-4,8,12-trimethyltrideca-3,7,11-trienoic acid or a salt thereof is in the range from 15:85 to 50:50, preferably 15:85 to 50:50.

The isomerization of the 3-(Z)-unsaturated carboxylic acid of the formula I-Z is carried out in accordance with the invention in the presence of a base. Suitable bases are selected from alkali metal carbonates, alkaline earth metal carbonates, alkali metal hydrogencarbonates, alkaline earth metal hydrogencarbonates, alkali metal phosphates, alkaline earth metal phosphates, amines, basic N-heteroaromatic systems, basic ion exchangers and mixtures thereof.

Suitable alkali metal carbonates are e.g. lithium, sodium or potassium carbonate. Suitable alkali metal hydrogencarbonates are e.g. lithium, sodium or potassium hydrogencarbonate. Suitable alkaline earth metal carbonates are e.g. calcium and magnesium carbonate. Suitable alkaline earth metal hydrogencarbonates are e.g. calcium and magnesium hydrogencarbonate. Suitable alkali metal phosphates are sodium and potassium phosphate. Suitable alkaline earth metal phosphates are magnesium and calcium phosphate. Suitable basic ion exchangers are e.g. basic anion exchangers having secondary or tertiary amino groups or quaternary ammonium groups or mixtures thereof. Particular preference hereinafter is given to alkali metal carbonates such as sodium and potassium carbonate.

Suitable amines are monoalkylamines, dialkylamines, trialkylamines, specifically a mono-($C_1$-$C_{20}$-alkyl)amine such as a mono-($C_1$-$C_{15}$-alkyl)amine, di-($C_1$-$C_{20}$-alkyl)amine such as a, di-($C_1$-$C_{15}$-alkyl)amine, tri-($C_1$-$C_{20}$-alkyl)amine such as a tri-($C_1$-$C_{15}$-alkyl)-amine, for example monomethylamine, dimethylamine, trimethylamine, monoethylamine, diethylamine, triethylamine, monopropylamine, dipropylamine, tripropylamine, dibutylamine, tributylamine, trihexylamine, dihexylamine, trioctylamine, tridecylamine, N,N-dimethylethylamine, dimethylpropylamine, N,N-diisopropylethylamine (Hünig's base), and cycloaliphatic amines such as dicyclohexylamine, N,N-dimethylcyclohexylamine and N,N-dimethyldodecylamine. Further examples of suitable amines are 1,4-diazabicyclo[2.2.2]octane (DABCO), 1,8-diazabicyclo[5.4.0]undec-7-ene (DBU), piperidine, a N-($C_1$-$C_6$-alkyl) piperidine such as N-methylpiperidine and N-ethylpiperidine, morpholine, a N-($C_1$-$C_6$-alkyl)morpholine such as N-ethylmorpholine and N-methylmorpholine. Further examples of suitable amines are piperazine and a 1-($C_1$-$C_4$-alkyl)piperazine. Suitable basic N-heteroaromatic systems are unsubstituted basic N-heteroaromatic systems such as pyridine, imidazole, a N-($C_1$-$C_6$-alkyl)imidazole such as N-methylimidazole and quinoline, and basic N-heteroaromatic systems bearing a substituent selected from $C_1$-$C_4$-alkyl, di-($C_1$-$C_4$-alkyl)amino and pyrrolidinyl at a carbon ring member such as 4-methylpyridine, 4-(1-pyrrolidinyl)pyridine and 4-dimethylaminopyridine.

Particular preference is given hereinafter to amines. Particular preference is given to trimethylamine, dimethylamine, monomethylamine, triethylamine, diethylamine, monoethylamine, tripropylamine, dipropylamine, tributylamine, dibutylamine, trihexylamine, dihexylamine, dicyclohexylamine, morpholine, piperidine, N,N-diisopropylethylamine and N-ethylpiperidine and mixtures thereof.

It is self-evident that it is also possible to use mixtures of two or more of the bases specified above.

In case that the starting material is a composition comprising the compound of the formula I-Z or a salt thereof and the compound of the formula I-E or a salt thereof, the base is typically used in an amount of equal to or more than 0.1 to 5 mol of base per mole of the total amount of the compound of the formula I-Z or a salt thereof and the compound of the formula I-E or a salt thereof. The base is preferably used in an amount of 0.2 to 3 mol of base per mole of the total amount of the compound of the formula I-Z and the compound of the formula I-E. If the pure Z-isomer of the formula I-Z or a salt thereof or a composition comprising the compound of the formula I-Z or a salt thereof is used, the base is typically used in an amount of 0.1 to 5 mol of base per mole of compound of the formula I-Z or a salt thereof.

In an embodiment of the invention, the isomerization of the 3-(Z)-unsaturated carboxylic acid I-Z is carried out in the presence of a base and an anhydride of an organic acid. Suitable organic acids are especially carboxylic acids and organic sulfonic acids. The anhydride is preferably selected from anhydrides of aliphatic $C_1$-$C_{12}$-monocarboxylic acids, anhydrides of aliphatic $C_4$-$C_{20}$-dicarboxylic acids, anhydrides of cycloaliphatic $C_7$-$C_{20}$-dicarboxylic acids, anhydrides of aromatic $C_8$-$C_{20}$-dicarboxylic acids, anhydrides of aliphatic sulfonic acids or anhydrides of aromatic sulfonic acids.

Suitable anhydrides of aliphatic $C_1$-$C_{12}$-monocarboxylic acids are the anhydrides of linear or branched monobasic $C_1$-$C_{12}$-alkanecarboxylic acids. Examples thereof are acetic anhydride, propionic anhydride, isopropionic anhydride, butyric anhydride, n-valeric anhydride, the mixed anhydride of formic acid and acetic acid and the like. Among these, the symmetrical anhydrides of alkanemonocarboxylic acids having up to 5 carbon atoms are preferred. These include further the anhydrides of linear or branched monobasic $C_3$-$C_{12}$-alkenecarboxylic acids. Examples thereof are (meth)acrylic anhydride, crotonic anhydride and isocrotonic anhydride. Examples of suitable anhydrides of aliphatic $C_4$-$C_{20}$-dicarboxylic acids are the anhydrides of linear or branched dibasic $C_4$-$C_{20}$-alkanecarboxylic acids, e.g. the anhydride of succinic acid, glutaric acid, adipic acid, pimelic acid, suberic acid, azelaic acid, sebacic acid, undecanedioic acid, dodecanedioic acid, brassylic acid, tetradecanedioic acid, pentadecanedioic acid, hexadecanedioic acid, heptadecanedioic acid, octadecanedioic acid. These include further the anhydrides of linear or branched dibasic $C_4$-$C_{20}$-alkene-carboxylic acids, e.g. maleic anhydride or itaconic anhydride. Suitable examples of anhydrides of cycloaliphatic $C_7$-$C_{20}$-dicarboxylic acids are cyclopentanedicarboxylic anhydride and cyclohexanecarboxylic anhydride. Likewise suitable are the anhydrides of aromatic $C_8$-$C_{20}$-dicarboxylic acids such as phthalic anhydride, 1,8-naphthalenecarboxylic anhydride or 2,3-naphthalenecarboxylic anhydride. Preference is given hereinafter to acetic anhydride, propionic anhydride, isopropionic anhydride, butyric anhydride, succinic anhydride, maleic anhydride and phthalic anhydride, especially acetic anhydride and maleic anhydride.

Also suitable are the anhydrides of organic sulfonic acids of the formula III

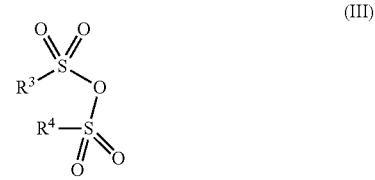

in which $R^3$ and $R^4$ are each independently $C_1$-$C_6$-alkyl, $C_1$-$C_6$-fluoroalkyl, phenyl, which is unsubstituted or is substituted by a substituent selected from bromine, nitro and $C_1$-$C_4$-alkyl.

In the anhydrides of the formula III, $R^3$ and $R^4$ preferably have the same definition. $R^3$ and $R^4$ are especially $C_1$-$C_4$-alkyl, $C_1$-$C_4$-fluoroalkyl and phenyl, which is unsubstituted or is substituted by a substituent selected from bromine, nitro and $C_1$-$C_4$-alkyl. Preference is given hereinafter to methanesulfonic anhydride, trifluoromethanesulfonic anhydride, phenylsulfonic anhydride, p-toluenesulfonic anhydride, 4-bromophenylsulfonic anhydride and 4-nitrophenylsulfonic anhydride, with methanesulfonic anhydride and p-toluenesulfonic anhydride being particularly preferred.

The anhydride can be used advantageously in a substoichiometric amount up to a stoichiometric amount, based on the total amount of the compounds of the formulae I-Z and I-E or salts thereof. Preference is given to using 0.05 to 0.8 mol of anhydride per mole of the total amount of the compound of the formula I-Z or a salt thereof and the compound of the formula I-E or a salt thereof. The anhydride is particularly used in an amount from 0.1 to 0.5 mol of anhydride per mole of the total amount of the compound I-Z or a salt thereof and the compound I-E or a salt thereof. If the pure Z-isomer of the formula I-Z or a salt thereof or a composition comprising the compound of the formula I-Z or a salt thereof is used, the anhydride is typically used in an amount from 0.1 to 0.5 mol of anhydride per mole of compound of the formula I-Z or a salt thereof.

In another embodiment of the invention, the isomerization of the 3-(Z)-unsaturated carboxylic acid I-Z is carried out in the presence of a base and a ketene of the formula V

(V)

wherein $R^{11}$ and $R^{12}$, independently of each other, are selected from hydrogen, linear or branched $C_1$-$C_{24}$-alkyl, $C_5$-$C_{12}$-cycloalkyl that is unsubstituted or substituted by 1, 2 or 3 $C_1$-$C_6$-alkyl radicals, or $C_6$-$C_{14}$-aryl that is unsubstituted or substituted by 1, 2 or 3 $C_1$-$C_6$-alkyl radicals.

Preferred are ketenes of the formula V, wherein $R^{11}$ and $R^{12}$ are independently of each other selected from hydrogen, $C_1$-$C_{10}$-alkyl and $C_{10}$-$C_{18}$-alkenyl having 1, 2 or 3 double bounds. Especially $R^{11}$ and $R^{12}$ are both hydrogen. Likewise especially preferred is the the ketene of homofarnesylic acid, i.e. a compound of formula V, wherein $R^{11}$ is hydrogen and $R^{12}$ is 2,6,10-trimethylundeca-1,5,9-trienyl.

The simplest representative of the ketene compound of the formula V is $CH_2$=C=O (ethenone). Ethenone is preferably generated by high temperature pyrolysis of acetone or acetic acid at temperatures generally higher than 650° C. The temperature for generating ethenone is preferably in the range from 650 to 1000° C., particularly preferably from 700 to 900° C.

In a specific embodiment, ethenone is prepared under reduced pressure. The pressure is preferably in the range from about 100 to 900 mbar, particularly preferably from 300 to 500 mbar, especially from 350 to 450 mbar. In an alternative embodiment, ethenone is prepared at ambient pressure ("unpressurized"). In this case, the pressure is preferably in the range from about 950 to 1050 mbar.

Methods and apparatuses for preparing ethenone are described, for example, in Organic Syntheses, Coll. Vol. 1, p. 330 (1941) and Vol. 4, p. 39 (1925) and in Chemiker Zeitung [The Chemists Journal] 97, No. 2, pages 67 to 73 (1979). If a ketene compound $CR^{11}R^{12}$=C=O of formula V is to be used in the method according to the invention, where $R^{11}$ and $R^{12}$ are different from hydrogen, the preparation may in principle be carried out by known methods. These include, for example, the elimination of hydrogen halide from carbonyl halides having an adjacent hydrogen. Such methods are described, for example, in Organikum, VEB Deutscher Verlag der Wissenschaften, $16^{th}$ Edition, Berlin 1986, Chapter 3.1.5, specifically page 234. The preparation of ketene compounds is also possible by way of the Arndt-Eistert synthesis by reacting a carbonyl halide with diazomethane.

Since ketene compounds of formula V and particularly ethenone are exceptionally reactive compounds which have a strong tendency to dimerize forming diketenes, a ketene compound is used in the method according to the invention which has preferably been prepared only briefly prior to use. The method according to the invention is rendered particularly advantageous when using ethenone which has been prepared directly prior to use, for example, by thermal cleavage of acetone, acetic acid or acetic anhydride or by dehydrochlorination of acetyl chloride using bases such as triethylamine.

The ketene of the formula V can be introduced via any suitable devices. Good distribution and rapid mixing are advantageous. Suitable devices are, for example, sparging lances which may be fixed in position, or preferably nozzles. The nozzles can be provided at or near the bottom of the reactor. For this purpose, the nozzles may be configured as openings from a hollow chamber surrounding the reactor. However, preference is given to using immersed nozzles with suitable feed lines. A plurality of nozzles can, for example, be arranged in the form of a ring. The nozzles may point upward or downward. The nozzles preferably point obliquely downward.

The ketene of formula V can be used advantageously in a substoichiometric amount up to a stoichiometric amount, based on the total amount of the compounds of the formulae I-Z and I-E or salts thereof. Preference is given to using 0.05 to 0.8 mol of ketene of formula V per mole of the total amount of the compound of the formula I-Z or a salt thereof and the compound of the formula I-E or a salt thereof. The ketene of formula V is particularly used in an amount from 0.1 to 0.5 mol per mole of the total amount of the compound I-Z or a salt thereof and the compound I-E or a salt thereof.

In a preferred embodiment in the method according to the invention, the isomerization is carried out in the presence of a base and an anhydride of an organic acid as described above.

The method according to the invention can be carried out either solvent-free or in an inert solvent or diluent. Examples of suitable diluents or solvents are particularly aliphatic hydrocarbons such as hexane, cyclohexane, heptane, octane; aromatic hydrocarbons such as toluene, xylene; dialkyl ethers such as methyl tert-butyl ether and diisopropyl ether. When carrying out the method without solvent, the anhydride and/or the base can serve as solvent or diluent.

The method according to the invention is typically conducted at a reaction temperature above 20° C. The method is preferably conducted at a temperature in the range from 60 to 175° C., especially in the range from 70 to 160° C.

The method according to the invention can be carried out at positive pressure, negative pressure or atmospheric pressure. The method according to the invention is carried out in a pressure reactor when using a base and/or an anhydride having a boiling point at standard pressure below the reaction temperature. The method according to the invention is typically carried out in a glass reactor or glass vessel when using a base and an anhydride of an organic acid or having a boiling point at standard pressure above the reaction temperature.

The method according to the invention is carried out in a pressure reactor when using a base and/or a ketene having a boiling point at standard pressure below the reaction temperature.

The method according to the invention is carried out preferably at a pressure of 1 to 25 bar, preferably 1.1 to 25 bar.

In particular, the method according to the invention is conducted at a temperature of 60 to 175° C. and a pressure of 1 to 25 bar, for example at 1.1 to 25 bar.

Suitable pressure-resistant reactors are known to those skilled in the art and are described, for example, in Ullmann's Encyclopedia of Industrial Chemistry, Vol. 1, 3rd edition, 1951, p. 769 ff. It may be advantageous to use an autoclave for the method according to the invention, which may be provided, if desired, with a stirring device and an inner lining.

The reaction time at a temperature in the range of 70 to 160° C. is typically in the range of 3 to 24 hours.

The method according to the invention can be carried out in the presence of atmospheric oxygen or carbon monoxide or optionally under a protective gas atmosphere.

The method according to the invention can also be carried out advantageously under the conditions for preparing 3-unsaturated carboxylic acids by carbonylation of allylic alcohols or acylated alcohols in the presence of a transition metal catalyst and in the presence of an anhydride of an organic acid. Such methods are described in WO 2018/153727.

The method according to the invention can be carried out—after at least partial separation of the 3-(E) isomer as described above, as a repeated batch process or as a continuous process.

The reaction mixture obtained can optionally be purified in order to remove by-products, e.g. by mixing with water, acid, aqueous solution of an acid or aqueous solution of a base, separating the phases and optionally purifying the crude product chromatographically or by distillation.

The invention is more particularly elucidated by the working examples which follow.

HPLC-Analysis:
Spectrometer: Agilent Series 1100
Column: Chiralpak AD-RH 5 μm 150*4.6 mm by Daicel®
Eluent: A: 0.1 vol % $H_3PO_4$ in water
B: 0.1 vol % $H_3PO_4$ in acetonitrile

| Time [min] | % B[#] | Flow rate [mL/min] |
|---|---|---|
| 0.0 | 40 | 1.2 |
| 25.0 | 70 | 1.2 |
| 30.0 | 100 | 1.2 |
| 40.0 | 100 | 1.2 |
| 30.1 | 40 | 1.2 |

[#]based on A + B = 100%

Detector: UV detector λ=205 nm, BW=5 nm
Flow rate: 1.2 mL/min
Injection: 5 μL
Temperature: 40° C.
Time: 45 min
Pressure: ca. 70 bar The following abbreviations used herein below have the following meaning:
homofarnesylic acid: 4,8,12,-trimethyltrideca-3,7,11-trienoic acid.
3Z,7E-homofarnesylic acid: (3Z,7E)-4,8,12-trimethyltrideca-3,7,11-trienoic acid.
3E,7E-homofarnesylic acid: (3E,7E)-4,8,12-trimethyltrideca-3,7,11-trienoic acid.
2E,7E-homofarnesylic acid: (2E,7E)-4,8,12-trimethyltrideca-2,7,11-trienoic acid.
$Ac_2O$: acetic anhydride.
eq: equivalent.

Example 1

Providing a Composition Comprising Homofarnesylic Acid

A steel autoclave was filled with palladium(II) acetate (46 mg, 0.2 mmol), triphenylphosphine (120 mg, 0.46 mmol) and 4-dimethylaminopyridine (DMAP, 56 mg, 0.46 mmol) under argon. (E)-Nerolidol (34 g, 152.6 mmol), triethylamine (17 g, 167 mmol) and acetic anhydride (3.6 g, 35 mmol) were added in argon countercurrent. 10 bar of CO were then applied and the mixture was stirred at 1000 rpm at this pressure at 70° C. internal temperature for 24 h. After 24 h, the mixture was cooled to room temperature and depressurized. GC analysis of the reaction output revealed a conversion of 95% at a selectivity of 81% for the products (3E,7-homofarnesylic acid, (2E,7-homofarnesylic acid) and (3Z,7E)-homofarnesylic acid.

After the reaction had ended, the crude product was purified by Kugelrohr distillation (1 mbar, up to 170° C.). This gave 23 g (61%) of E/Z-homofarnesylic acid with a purity (GC) of 97% with an isomer ratio of (3E,7E-homofarnesylic acid and 2E,7E-homofarnesylic acid):(3Z,7E-homofarnesylic acid) equal to 64:36 (GC).

The resulting mixture was dissolved in n-heptane (100 g), to which isopropanol (10 g) and Novozym 435 (0.5 g) were added and the mixture was stirred at 60° C. for ca. 17 h. The enzyme was then filtered off. At a temperature of 0° C., methanol and water were added and the pH of the reaction mixture was adjusted to pH 12-13 by adding aqueous NaOH at a temperature below 10° C. The phases were separated yielding an organic phase with (3E,7E)-homofarnesylic acid isopropyl ester as main component and an aqueous phase having a composition comprising 3Z,7E-homofarnesylic acid:3E,7E-homofarnesylic acid:2E,7E-homofarnesylic acid:other compounds in a ratio of 68%:14%:17%:1% (HPLC). This composition was used in the following working examples.

Example 2

A steel autoclave was loaded with palladium(II) acetate (22 mg, 0.098 mmol), triphenylphosphine (58 mg, 0.22 mmol) and 4-dimethylaminopyridine (25 mg, 0.2 mmol) under argon. A composition comprising (3E,7E)-homofarnesylic acid, (2E,7E)-homofarnesylic acid) and (3Z,7E)-homofarnesylic acid according to Example 1 (17.5 g), triethylamine (8.1 g, 80 mmol) and acetic anhydride (1.7 g, 17 mmol) were added in the argon countercurrent and 20 bar of CO were applied. The mixture was then stirred at 140° C.

internal temperature for 14 h (1000 rpm). The pressure was kept constant at 20 bar. The mixture was then cooled to room temperature and depressurized. This gave a composition comprising 3Z,7E-homofarnesylic acid:3E,7E-homofarnesylic acid:2E,7E-homofarnesylic acid:other compounds in a ratio of 22%:33%:21%:24% (HPLC).

Example 3

A steel autoclave was loaded with a composition comprising (3E,7E)-homofarnesylic acid, (2E,7E)-homofarnesylic acid) and (3Z,7E)-homofarnesylic acid according to Example 1 (35 g), triethylamine (16 g, 158 mmol) and acetic anhydride (3.4 g, 33 mmol) under 20 bar of CO. The mixture was stirred at 140° C. internal temperature for 14 h (1000 rpm). The mixture was then cooled to room temperature and depressurized. The resulting composition comprised 3Z,7E-homofarnesylic acid:3E,7E-homofarnesylic acid:2E,7E-homofarnesylic acid:other compounds in a ratio of 22%:34%:21%:23% (according to HPLC).

Example 4a

Isomerization of a Mixture at 3 Bar Nitrogen Using Triethylamine as Base

A steel autoclave was loaded with a composition comprising (3E,7E)-homofarnesylic acid, (2E,7E)-homofarnesylic acid) and (3Z,7E)-homofarnesylic acid according to Example 1 (17.5 g), triethylamine (8 g, 79 mmol) and acetic anhydride (1.7 g, 16 mmol) under 3 bar of nitrogen. The mixture was stirred at 140° C. internal temperature for 14 h (1000 rpm). The mixture was then cooled to room temperature and depressurized. The resulting composition comprised 3Z,7E-homofarnesylic acid:3E,7E-homofarnesylic acid:2E,7E-homofarnesylic acid:other compounds in a ratio of 20%:29%:23%:28% (according to HPLC).

Example 4b

Isomerization of a Mixture at 3 Bar Nitrogen Using Diisopropyethylamine as Base

A steel autoclave was loaded with a composition comprising (3E,7E)-homofarnesylic acid, (2E,7E)-homofarnesylic acid) and (3Z,7E)-homofarnesylic acid according to Example 1 (17.5 g), diisopropylethylamine (10 g, 78 mmol) and acetic anhydride (1.7 g, 16 mmol) under 3 bar of nitrogen. The mixture was stirred at 140° C. internal temperature for 14 h (1000 rpm). The mixture was then cooled to room temperature and depressurized. The resulting composition comprised 3Z,7E-homofarnesylic acid:3E,7E-homofarnesylic acid:2E,7E-homofarnesylic acid:other compounds in a ratio of 22%:31%:24%:23% (according to HPLC).

Example 4c

Isomerization of a Mixture at 3 Bar Nitrogen Using N-Ethylpiperidine as Base at 140° C.

A steel autoclave was loaded with a composition comprising (3E,7E)-homofarnesylic acid, (2E,7E)-homofarnesylic acid) and (3Z,7E)-homofarnesylic acid according to Example 1 (17.5 g), N-ethylpiperidine (9 g, 79 mmol) and acetic anhydride (1.7 g, 16 mmol) under 3 bar of nitrogen. The mixture was stirred at 140° C. internal temperature for 14 h (1000 rpm). The mixture was then cooled to room temperature and depressurized. The resulting composition comprised 3Z,7E-homofarnesylic acid:3E,7E-homofarnesylic acid:2E,7E-homofarnesylic acid:other compounds in a ratio of 22%:33%:23%:22% (according to HPLC).

Example 4d

Isomerization of a Mixture at 3 Bar Nitrogen Using N-Ethylpiperidine as Base at 120° C.

A steel autoclave was loaded with a composition comprising (3E,7E)-homofarnesylic acid, (2E,7E)-homofarnesylic acid) and (3Z,7E)-homofarnesylic acid according to Example 1 (17.5 g), N-ethylpiperidine (9 g, 79 mmol) and acetic anhydride (1.7 g, 16 mmol) under 3 bar of nitrogen. The mixture was stirred at 120° C. internal temperature for 14 h (1000 rpm). The mixture was then cooled to room temperature and depressurized. The resulting composition comprised 3Z,7E-homofarnesylic acid:3E,7E-homofarnesylic acid:2E,7E-homofarnesylic acid:other compounds in a ratio of 24%:35%:26%:15% (according to HPLC).

Example 4e

Isomerization of a Mixture at 3 Bar Nitrogen Using N-Ethylpiperidine as Base at 100° C.

A steel autoclave was loaded with a composition comprising (3E,7-homofarnesylic acid, (2E,7-homofarnesylic acid) and (3Z,7E)-homofarnesylic acid according to Example 1 (17.5 g), N-ethylpiperidine (9 g, 79 mmol) and acetic anhydride (1.7 g, 16 mmol) under 3 bar of nitrogen. The mixture was stirred at 100° C. internal temperature for 14 h (1000 rpm). The mixture was then cooled to room temperature and depressurized. The resulting composition comprised 3Z,7E-homofarnesylic acid:3E,7E-homofarnesylic acid:2E,7E-homofarnesylic acid:other compounds in a ratio of 29%:32%:26%:13% (according to HPLC).

Examples 4f1-4f4

Isomerization of a Mixture Using N-Ethylpiperidine as Base in Different Concentrations and in the Presence or Absence of the Solvent Xylene A typical experimental procedure for examples 4f1-4f4 is described below for example 4f1.

Example 4f1

A closed 25 mL glass flask was charged with a composition comprising (3E:7E)-homofarnesylic acid, (2E,7E-homofarnesylic acid) and (3Z,7E)-homofarnesylic acid according to Example 1 (5.0 g), N-ethylpiperidine (2.5 g, 22 mmol=1.5 eq) and acetic anhydride (0.5 g, 4.9 mmol). The mixture was heated at the specified internal temperature as indicated in table 1 below and stirred for 14 hours. The mixture was then cooled to room temperature. The resulting composition comprised 3E,7E-homofarnesylic acid:3Z,7E-homofarnesylic acid:2E,7E-homofarnesylic acid:other compounds in a ratio of 32%:22%:23%:23% (according to HPLC).

Examples 4f2-4f4 were carried out analogously to example 4f1 except that the concentration of N-ethylpiperidine and/or internal temperature were modified as indicated in table 1 below. In addition, examples 4f2 and 4f3 were carried out in the presence of a solvent as indicated in table 1 below.

TABLE 1

Isomerization of a composition comprising (3E,7E)-homofarnesylic acid, (2E,7E)-homofarnesylic acid) and (3Z,7E)-homofarnesylic acid according to Example 1 in the presence of acetic anhydride/N-ethylpiperidine and in the presence or absence of a solvent using various concentrations of N-ethylpiperidine

| Example | N-ethyl-piperidine [eq.] | Solvent [g] | internal temperature [° C.] | 3E,7E-homofarnesylic acid:3Z,7E-homofarnesylic acid:2E,7E-homofarnesylic acid:other compounds [ratios in %] |
|---|---|---|---|---|
| 4f1 | 1.5 | — | 120 | 32:22:23:23 |
| 4f2 | 0.75 | xylene (1.2) | 120 | 32:25:24:19 |
| 4f3 | 0.5 | xylene (1.2) | 115 | 30:27:24:19 |
| 4f4 | 0.5 | — | 115 | 29:23:22:26 |

Example 5

A steel autoclave was loaded with a composition comprising (3E,7E)-homofarnesylic acid, (2E,7E)-homofarnesylic acid) and (3Z,7E)-homofarnesylic acid according to Example 1 (17.5 g), triethylamine (8 g, 79 mmol) and acetic anhydride (0.5 g, 5 mmol) under 20 bar of CO. The mixture was stirred at 140° C. internal temperature for 14 h (1000 rpm). The mixture was then cooled to room temperature and depressurized. The resulting composition comprised 3Z,7E-homofarnesylic acid:3E,7E-homofarnesylic acid:2E,7E-homofarnesylic acid:other compounds in a ratio of 28%:29%:27%:16% (according to HPLC).

Example 6

A steel autoclave was loaded with a composition comprising (3E,7E)-homofarnesylic acid, (2E,7E)-homofarnesylic acid) and (3Z,7E)-homofarnesylic acid according to Example 1 (17.5 g), triethylamine (1 g, 9.9 mmol) and acetic anhydride (1.7 g, 16 mmol) under 20 bar of CO. The mixture was stirred at 140° C. internal temperature for 14 h (1000 rpm). The mixture was then cooled to room temperature and depressurized. The resulting composition comprised 3Z,7E-homofarnesylic acid:3E,7E-homofarnesylic acid:2E,7E-homofarnesylic acid:other compounds in a ratio of 20%:22%:25%:33% (according to HPLC).

Example 7

A steel autoclave was loaded with a composition comprising (3E,7E-homofarnesylic acid, (2E,7E)-homofarnesylic acid) and (3Z,7E)-homofarnesylic acid according to Example 1 (17.5 g), triethylamine (8.1 g, 80 mmol) and acetic anhydride (1.7 g, 17 mmol) under 20 bar of CO. The mixture was stirred (1000 rpm) at 100° C. internal temperature for 14 h, the pressure being kept constant at 20 bar. The mixture was then cooled to room temperature and depressurized. The resulting composition comprised 3Z,7E-homofarnesylic acid:3E,7E-homofarnesylic acid:2E,7E-homofarnesylic acid:other compounds in a ratio of 20%:22%:26%:32% (according to HPLC).

Example 8

Isomerization of a Mixture in the Absence of Anhydride

A steel autoclave was loaded with a composition comprising (3E,7-homofarnesylic acid, (2E,7-homofarnesylic acid) and (3Z,7E)-homofarnesylic acid according to Example 1 (17.5 g) and triethylamine (8 g, 79 mmol) under 20 bar of CO. The mixture was stirred at 140° C. internal temperature for 14 h (1000 rpm). The mixture was then cooled to room temperature and depressurized. The resulting composition comprised 3Z,7E-homofarnesylic acid:3E,7E-homofarnesylic acid:2E,7E-homofarnesylic acid:other compounds in a ratio of 42%:7%:19%:30% (according to HPLC).

Example 9

Isomerization in the Presence of Acetic Acid in Place of Acetic Anhydride

A steel autoclave was loaded with a composition comprising (3E,7-homofarnesylic acid, (2E,7-homofarnesylic add) and (3Z,7E)-homofarnesylic acid according to Example 1 (17.5 g), triethylamine (8 g, 79 mmol) and acetic acid (1 g, 16.6 mmol) under 3 bar of nitrogen. The mixture was stirred at 140° C. internal temperature for 14 h (1000 rpm). The mixture was then cooled to room temperature and depressurized. The resulting composition comprised 3Z,7E-homofarnesylic acid:3E,7E-homofarnesylic acid:2E,7E-homofarnesylic acid:other compounds in a ratio of 44%:18%:23%:15% (according to HPLC).

Example 10

Comparative Example of Purely Thermal Means

A steel autoclave was loaded with a composition comprising (3E,7-homofarnesylic add, (2E,7-homofarnesylic add) and (3Z,7E)-homofarnesylic acid according to Example 1 (17.5 g) and the composition was stirred (1000 rpm) at 140° C. internal temperature for 24 h. The mixture was then cooled to room temperature and depressurized. The ratio of 3Z,7E-homofarnesylic acid:3E,7E-homofarnesylic acid:2E,7E-homofarnesylic acid:other compounds used in the composition of the starting mixture remained unchanged.

The invention claimed is:
1. A method for isomerizing a 3-(Z)-unsaturated carboxylic acid of the formula I-Z

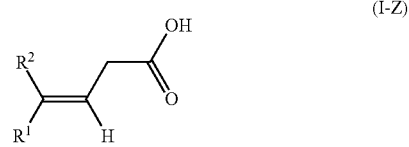

or a salt thereof,
in which
R[1] is hydrogen, linear or branched $C_1$-$C_{24}$-alkyl, linear or branched $C_2$-$C_{24}$-alkenyl having 1, 2, 3 or more than 3 C—C double bonds, $C_5$-$C_{12}$-cycloalkyl that is unsubstituted or substituted by 1, 2 or 3 $C_1$-$C_6$-alkyl radicals, or $C_6$-$C_{20}$-aryl that is unsubstituted or substituted by 1, 2 or 3 $C_1$-$C_6$-alkyl radicals;
and
$R^2$ is linear or branched $C_1$-$C_{24}$-alkyl, linear or branched $C_2$-$C_{24}$-alkenyl having 1, 2, 3 or more than 3 C—C double bonds, $C_5$-$C_{12}$-cycloalkyl that is unsubstituted or substituted by 1, 2 or 3 $C_1$-$C_6$-alkyl radicals, or $C_6$-$C_{20}$-aryl that is unsubstituted or substituted by 1, 2 or 3 $C_1$-$C_6$-alkyl radicals;
with the proviso that $R^2$ has a higher priority than $R^1$ in accordance with IUPAC;
to give a 3-(E)-unsaturated carboxylic acid of the formula I-E

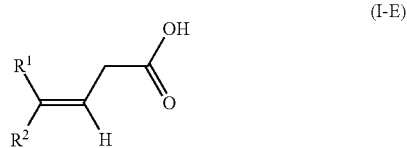

(I-E)

or a salt thereof;
wherein the isomerization of the compound of the formula I-Z or a salt thereof is effected in the presence of an anhydride of an organic acid and a base.

2. The method according to claim 1, wherein a composition is used comprising the compound of the formula I-Z or a salt thereof and the compound of the formula I-E or a salt thereof, and the compound of the formula I-Z or a salt thereof is isomerized to the compound of the formula I-E or a salt thereof, wherein a composition is obtained in which the content of compound of the formula I-E is increased compared to the content of compound I-E in the composition used.

3. The method according to claim 2, wherein the ratio by weight in the composition used of the compounds I-Z or a salt thereof to the compound I-E or a salt thereof is greater than 50:50.

4. The method according to claim 2, wherein the composition used comprises (3Z,7E)-4,8,12-trimethyltrideca-3,7,11-trienoic acid as compound of the formula I-Z and (3E,7E)-4,8,12-trimethyltrideca-3,7,11-trienoic acid as compound of the formula I-E.

5. The method according to claim 4, which comprises the following steps:
(a) providing a first composition comprising (3Z,7E)-4,8,12-trimethyltrideca-3,7,11-trienoic acid and (3E,7E)-4,8,12-trimethyltrideca-3,7,11-trienoic acid;
(b) subjecting the first composition from step (a) to an enzyme-catalyzed esterification in the presence of an alcohol and a lipase enzyme, to obtain a composition comprising (3E,7E)-4,8,12-trimethyltrideca-3,7,11-trienoic acid ester, unreacted (3E,7E)-4,8,12-trimethyltrideca-3,7,11-trienoic acid and unreacted (3Z,7E)-4,8,12-trimethyltrideca-3,7,11-trienoic acid; and
(c) separating off a composition comprising (3E,7E)-4,8,12-trimethyltrideca-3,7,11-trienoic acid ester from the composition obtained in step (b), and obtaining a second composition comprising (3Z,7E)-4,8,12-trimethyltrideca-3,7,11-trienoic acid and (3E,7E)-4,8,12-trimethyltrideca-3,7,11-trienoic acid, wherein the content of (3Z,7E)-4,8,12-trimethyltrideca-3,7,11-trienoic acid in the second composition is increased compared to the first composition provided in step (a);
where the second composition obtained in step (c) is subjected to the isomerization.

6. The method according to claim 4, which comprises the following steps:
(d) providing a composition comprising (3E,7E)-4,8,12-trimethyltrideca-3,7,11-trienoic acid ester and (3Z,7E)-4,8,12-trimethyltrideca-3,7,11-trienoic acid-ester in a ratio by weight from 80:20 to 50:50;
(e) subjecting the composition provided in step (d) to an enzyme-catalyzed ester cleavage in the presence of a lipase enzyme to obtain a composition comprising (3E,7E)-4,8,12-trimethyltrideca-3,7,11-trienoic acid, unreacted (3E,7E)-4,8,12-trimethyltrideca-3,7,11-trienoic acid ester and unreacted (3Z,7E)-4,8,12-trimethyltrideca-3,7,11-trienoic acid ester;
(f) separating off a composition comprising (3E,7E)-4,8,12-trimethyltrideca-3,7,11-trienoic acid from the composition obtained in step (e) and obtaining a composition comprising (3Z,7E)-4,8,12-trimethyltrideca-3,7,11-trienoic acid ester and (3E,7E)-4,8,12-trimethyltrideca-3,7,11-trienoic acid ester; and
(g) subjecting the composition obtained in step (f), comprising (3Z,7E)-4,8,12-trimethyltrideca-3,7,11-trienoic acid ester and (3E,7E)-4,8,12-trimethyltrideca-3,7,11-trienoic acid ester, an ester cleavage to obtain a composition-comprising (3Z,7E)-4,8,12-trimethyltrideca-3,7,11-trienoic acid or a salt-thereof and (3E,7E)-4,8,12-trimethyltrideca-3,7,11-trienoic acid or a salt thereof in a ratio by weight greater than 50:50.

7. The method according to claim 4, wherein the composition used for the isomerization comprises (3E,7E)-4,8,12-trimethyltrideca-3,7,11-trienoic acid or a salt thereof and (3Z,7E)-4,8,12-trimethyltrideca-3,7,11-trienoic acid or a salt thereof in a ratio by weight from 1:99 to 50:50.

8. The method according to claim 1, wherein the method is conducted at a temperature in the range from 60 to 175° C.

9. The method according to claim 1, wherein the base is selected from alkali metal carbonates, alkaline earth metal carbonates, alkali metal hydrogencarbonates, alkaline earth metal hydrogencarbonates, alkali metal phosphates, alkaline earth metal phosphates, amines, basic N-heteroaromatic systems, basic ion exchangers and mixtures thereof.

10. The method according to claim 9, wherein the base is an amine selected from trimethylamine, dimethylamine, monomethylamine, triethylamine, diethylamine, monoethylamine, tripropylamine, dipropylamine, tributylamine, dibutylamine, trihexylamine, dihexylamine, dicyclohexylamine, morpholine, piperidine, N,N-diisopropylethylamine, N-ethylpiperidine or mixtures thereof.

11. The method according to claim 1, wherein 0.1 to 5 mol of base is used per mole of the compound of the formula I-Z or a salt thereof and the compound of the formula I-E or a salt thereof.

12. The method according to claim 1, wherein the anhydride is selected from anhydrides of aliphatic C1-C12-monocarboxylic acids, anhydrides of aliphatic C4-C20-dicarboxylic acids, anhydrides of cycloaliphatic C7-C20-dicarboxylic acids, anhydrides of aromatic C8-C20-dicarboxylic acids, anhydrides of aliphatic sulfonic acids, anhydrides of aromatic sulfonic acids, acetic anhydride, maleic anhydride, p-toluenesulfonic anhydride and methanesulfonic anhydride.

13. The method according to claim 1, wherein 0.05 to 0.8 mol of anhydride is used per mole of the compound I-Z or a salt thereof and the compound I-E or a salt thereof.

* * * * *